United States Patent [19]
Nishida et al.

[11] Patent Number: 5,855,888
[45] Date of Patent: Jan. 5, 1999

[54] DRUG FOR THE TREATMENT OF RHEUMATOID ARTHRITIS

[75] Inventors: Tadashi Nishida, Osaka; Sachiko Miyake; Hideo Yagita, both of Tokyo; Ko Okumura, Chiba, all of Japan

[73] Assignee: Kanebo, Ltd., Tokyo, Japan

[21] Appl. No.: 727,406

[22] PCT Filed: Mar. 22, 1995

[86] PCT No.: PCT/JP95/00527

§ 371 Date: Oct. 17, 1996

§ 102(e) Date: Oct. 17, 1996

[87] PCT Pub. No.: WO95/28961

PCT Pub. Date: Nov. 2, 1995

[30] Foreign Application Priority Data

Apr. 26, 1994 [JP] Japan .................................. 6-088251

[51] Int. Cl.$^6$ .......................... A61K 39/395; C07K 16/28
[52] U.S. Cl. .................................... 424/156.1; 424/133.1; 424/141.1; 424/143.1; 424/144.1; 424/152.1; 424/154.1; 530/387.3; 530/388.2; 530/388.22; 530/388.73; 530/388.75; 530/388.85; 530/389.6
[58] Field of Search .............................. 530/388.2, 387.3, 530/387.1, 388.22, 388.73, 388.75, 388.85, 389.6; 424/133.1, 141.1, 130.1, 143.1, 144.1, 152.1, 154.1, 156.1

[56] References Cited

U.S. PATENT DOCUMENTS 5,583,203  12/1996  Hemler .

FOREIGN PATENT DOCUMENTS

WO92/00751  1/1992  WIPO .
WO 93/02108  2/1993  WIPO .

OTHER PUBLICATIONS

Panayi, et al., "The Importance of the T Cell in Initiating and Maintaining the Chronic Synovitis of Rheumatoid Arthritis", *Arth. Rheum.*, vol. 35, No. 7, 1992, pp. 729–735.
Kakimoto, et al., "The Effect of Anti–Adhesion Molecule Antibody on the Development of Collagen–Induced Arthritis", *Cell Immunol.*, 142, 1992, pp. 326–337.
Kakimoto, et al., "Suppression of Collagen–Induced Arthritis by Clonal Anergy produced by Co–administration of Monoclonal Antibodies to LFA–1 and ICAM–1", *Japan Immunological Assoc., General Assembly Documents*, 23, 1–28 (1993), p. 530.
Durie, et al., "Prevention of Collagen–Induced Arthritis with an Antibody to gp39, the Ligand for DC40", *Science*, Vo. 261, Sep. 1993, pp. 1328–1330.

Miyake, et al., "β1 Integrin–mediated Interaction with Extracellular Matrix Proteins Regulates Cykokine Gene Expression in Synovial Fluid Cells of Rheumatoid Arthritis Patients", *J. Exp. Med.*, vol. 177, Mar. 1993, pp. 863–868.
Haynes, et al., "The Role of Leukocyte Adhesion Molecules in Cellular Interactions: Implications for the Pathogenesis of Inflammatory Synovitis", *Springer Semin. Immunopathol.*, vol. 11, 1989, pp. 163–185.
Pischel, et al., Use of the Monoclonal Antibody 12F1 to Characterize the Differentiation Antigen VLA–2$^1$, *J. Immunol.*, vol. 138, 1987, pp. 226–233.
Carter, et al., The Role of Integrins α2β1 and α3β1 in Cell–Cell and Cell–Substrate Adhesion of Human Epidermal Cells, *J. Cell Biol.*, vol. 110, Apr. 1990, pp. 1387–1404.
Milstein, et al., Continuous cultures of fused cells secreting antibody of predefined specificity:, *Nature*, vol. 256, Aug. 1975, p. 495.
Queen, et al., "A humanized antibody that binds to the interleukin 2 receptor", *Proc. Natl., Acad. Sci.*, vol. 86, Dec. 1989, pp. 10029–10033.
Jackson, et al., "Possible mechanisms of type 1 collagen–induced vascular tube formation", *Experiential. Suppl.*, vol. 61, Angiogenesis, 1992, pp. 198–204.
Berger, et al., Modulation of T lymphocyte function by the angiogenesis inhibitor AGM–1470, *Agents Actions*, vol. 39 (Special Conf. Issue) 1993, pp. C86–C88.
European Journal of Immunology vol. 22, 1992, pp. 1109–1114, Goldman et al., "VLA–2 is the integrin used as a collagen receptor by leukocytes".
Reichmann, Nature 332:323, 1998.
Harlow & Lowe, "Antibodies: A Laboratory Manual," p. 287 Cold Spring Harbor Laboratory, 1988.
Durie Clinical Immunol and Immunopathol. 73: 11–18, 1994.
Ward, Therapeutic Immunology 1:164, 1994.
Stuart, Laboratory Investigation 54:1, 1986.
Morrison, Science 229:1202, 1985.
Sevear, Gen Eng News 14: pp. 10–21, 1994.

*Primary Examiner*—Toni R. Scheiner
*Assistant Examiner*—Nancy A. Johnson
*Attorney, Agent, or Firm*—Merchant, Gould, Smith, Edell, Welter & Schmidt

[57] ABSTRACT

A drug for the treatment of rheumatoid arthritis, which comprises as an active ingredient a monoclonal antibody which recognizes specifically extracellular region of human VLA-2. Preferable drug for the treatment of rheumatoid arthritis comprises as an active ingredient a monoclonal antibody which recognizes specifically extracellular region of human VLA-2, α chain. The above drug for the treatment of rheumatoid arthritis can suppress swelling due to arthritis in rheumatoid arthritis with low toxicity and hence is useful for the treatment of rheumatoid arthritis.

6 Claims, No Drawings

DRUG FOR THE TREATMENT OF RHEUMATOID ARTHRITIS

This application is a 371 of PCT/JP95/00527 filed Mar. 22, 1995.

DESCRIPTION

1. Technical Field

This invention relates to a drug for the treatment of rheumatoid arthritis which comprises as an active ingredient a monoclonal antibody which can specifically recognize extracellular region of human VLA-2.

2. Technical Background

Rheumatoid arthritis (hereinafter, abbrebiated as "RA") is a chronic inflammatory disease which shows an inflammatory symptom mainly in the articular synovial membrane, where various inflammatory cells permeate into synovial fluid through hemangioendotheliocytes of synovial membrane. It is assumed that the pathological symptoms may be participated by immunological mechanism, and the symptoms may become a trigger of immuno-response, but it is still difficult to specify the mechanism. It is also important to make clear the reason why the inflammatory symptoms are maintained at the synovial membrane even after the cause of the disease has been removed. A series of processes of these inflammation symptoms, particularly chronicity and duration thereof, will be deeply participated by lymphocytes which take charge of immunization.

Panayi, G. S. et al mentioned as "Synovitis (associated with RA) is no longer conceived as an antibody-mediated process involving rheumatoid factors and immune complexes, but rather as a cell-mediated process involving T cells, antigen-presenting cells (APC), macrophages, synoviocytes, and cytokines." (cf. Arth. Rheum., 35, pp.729–735, 1992).

Kakimoto, K. et al. reported that when an anti-ICAM-1 antibody or anti-LFA-1 antibody was administered to a model of mouse suffered from collagen-induced arthritis (hereinafter abbreviated as "CIA") from the stage of the first sensitization with an antigen which is induction phase of arthritis, the CIA was suppressed in all cases [Cell. Immunol., 142, pp.326–337 (1992)]. It was further reported by Kakimoto et al. at the 23rd General Assembly of Japan Immunological Association that when a combination of an anti-ICAM-1 antibody and an anti-LFA-1 antibody was administered from the stage of the first sensitization with an antigen, the CIA was more effectively suppressed in rats in comparison with the administration of only either one of those antibodies [Japan Immunological Association, General Assembly Documents, 23, p.530, 1–28 (1993)].

Besides, Durie, F. H. et al. reported that in a mouse CIA model, CIA was suppressed by the administration of anti-CD 40 ligand (CD40L) antibody from the stage of the induction phase of arthritis [Science, 261, pp.1328–1330 (1993)].

On the other hand, it has been considered that collagen, fibronectin, laminin and proteoglycan, which are matrix molecules in synovial tissue, participate in fixation and retention of lymphocytes and macrophage into the tissue or activation thereof via VLA family. These participate deeply in the lesion of synovial membrane in RA, and hence, the clearance of the mechanism thereof is important for finding a suitable means of the treatement of RA.

Miyake, S. et al. have investigated the change of mRNA of cytokines where monocytes separated from the synovial fluid of RA patients were cultured on an immobilized matrix molecule overnight and the RNA was extracted, and then have found that their message was reduced by the anti-$\beta$1 integrin antibody [J. Exp. Med., 177, pp.863–868 (1993)]. Accordingly, it is considered that the matrix molecule will function as a co-stimulatory factor of lymphocytes.

The interaction between matrix molecule and cells will be participated by mainly integrin molecule and by other various molecules such as CD26 and CD44. Haynes et al. reported that adhesive molecules of VLA family exist widely in cells of synovial tissue such as Type A synovial cells, vessel endothelial cells, macrophage [Springer Semin. Immunopathol., 11, p.163 (1989)].

It is known that the adhesion molecules of the VLA family include VLA-1, -2, -3, -4, -5 and -6, in each of which the $\beta$1 chain and a chain ($\alpha$1, $\alpha$2, $\alpha$3, $\alpha$4, $\alpha$5, or $\alpha$6) are non-covalently bound each other to form heterodimers, wherein $\alpha$4 may also associate with $\beta$7 and $\alpha$6 may also associate with $\beta$4, and hence, it will be understood that $\alpha 4 \beta 7$ and $\alpha 6 \beta 4$ also belong to VLA family.

DISCLOSURE OF THE INVENTION

The present inventors have studied the treatment of RA by utilizing a monoclonal antibody which can recognize a certain adhesion factor and investigated various monoclonal antibodies with a mouse CIA model which is known to be close to human RA and have found that a certain monoclonal antibody shows the desired effects. An object of the invention is to provide a drug for the treatment of rheumatoid arthritis (hereinafter, referred to "RA treating drug") which comprises as an active ingredient a monoclonal antibody which can recognize a certain adhesion factor.

As a result of investigation as mentioned above, the present inventors have found that a monoclonal antibody which can specifically recognize extracellular region of human VLA-2 exhibits curative effects on the RA and hence is suitable for the above object.

That is, the present invention relates to a drug for the treatment of rheumatoid arthritis which comprises as an active ingredient a monoclonal antibody which can specifically recognize the extracellular region of human VLA-2.

BEST MODE FOR CARRYING OUT THE INVENTION

The present invention is explained in detail below.

The antibody used in the present invention includes any monoclonal antibody which can specifically recognize the extracellular region of human VLA-2, but a preferable monoclonal antibody is the one which can specifically recognize the extracellulor region of a chain of human VLA-2.

Besides, the above monoclonal antibody used in the present invention may be any one of mammalian origin antibodies, chimeric antibodies or humanized antibodies.

The mammalian antibodies used in the present invention have been known, for example in Ken D. Pischel et al., J. Immunol., 138, pp. 226–233 (1987), and William G. Carter et al., J. Cell Biol., 110, pp. 1387–1404 (1990).

The following antibodies are readily available and useful.

Anti-human VLA-2 antibody [anti-human $\alpha$2 monoclonal antibody: Clone P1E6 (CP10: a product of Oncogene Science, A042: a product of Terios Co., MAB 1950: a product of Chemicon Co.]; anti human-$\alpha 2 \beta 1$ monoclonal antibody: no disclosure of clone [MAB 1967: a product of Chemicon Co.].

For producing a chimeric antibody used in the present invention, a hybridoma being capable of producing the above-mentioned mouse anti-human monoclonal antibody is firstly prepared by the following procedure.

That is, cells reactive to the above anti-human VLA-2 antibody are separated from human lymphocytes selected from the group consisting of human memory T cells, human monocytes and human B cell lyphoma by flow cytometry (it is considered that the cells thus separated would have expressed an antigen against human VLA-2). The cells separated as mentioned above are suspended in a phosphate buffered saline solution, etc. and a mouse is immunized with said suspension by intravenous or intraperitoneal administration thereof, and then, the spleen is isolated from the immunized animal to prepare antibody-producing splenocytes. The antibody-producing splenocytes obtained from the immunized animal are subjected to cell fusion with myeloma cells. The myeloma cells are preferably mouse-origin cells. The cell fusion is carried out in a similar manner as disclosed by Milstein C. et al. [Nature, 256, p. 495 (1975)], that is, by reacting at a temperature of 30° C. to 40° C. for about 1 to 3 minutes using 30% to 60% polyethylene glycol (average molecular weight 1,000–4,000). By screening the monoclonal antibodies produced by the hybridomas thus prepared, the desired hybridoma being capable of producing a monoclonal antibody which can specifically recognize the human VLA-2 (antigen) is selected by utilizing flow cytometry.

From the thus-separated hybridoma being capable of producing a mouse anti-human monoclonal antibody, there are prepared mRNA and then cDNA library by a conventional method. From the library, a cDNA having the desired size is cloned by a conventional PCR reaction with a primer to a nucleotide sequence moiety common to a mouse antibody heavy chain region and light chain region. The thus obtained heavy chain region DNA segment or light chain region DNA segment coding for a mouse antibody variable region is conjugated precisely with a DNA segment coding for a human antibody constant region with preventing any amino acid substitution and flame shifting to give a chimeric antibody DNA.

The heavy chain DNA segment or light chain DNA segment of the chimeric antibody thus obtained is recombined into a known antibody expression vector respectively and simultaneously transfected to an appropriate host cell such as mouse myeloma cells to give a chimeric antibody-producing clone.

The clone is checked whether it can produce the desired antibody by screening the culture supernatant of the clone by ELISA or the like. Thereafter, the clone being capable of producing effectively mouse-human chimeric antibody is cultured, and the mouse-human chimeric antibody thus produced is isolated and purified from the culture broth with a protein G column. Finally, the antibody is subjected to gel filtration or dialysis to prepare a solution of the mouse-human chimeric antibody in a phosphate buffered saline solution.

The humanized antibody used in the present invention can be prepared in a similar manner as disclosed by Cary Queen et al. [Proc. Natl. Acad. Sci., 86, pp.10029–10033 (1989)], i.e. by determining the nucleotide sequence of the complementarity determining region (CDR) of the mouse anti-human antibody producing hybridoma DNA fragment, transplanting said region to a complementarity determining region of an appropriate human antibody to give a humanized antibody DNA. When any strain is formed in the three dimensional structure of the complementarity determining region during the above procedure, it may be corrected by replacing appropriately the base in the framework region.

The heavy chain DNA segment or light chain DNA segment of the humanized antibody thus obtained is recombined into a known antibody expression vector respectively and simultaneously transfected to an appropriate host cell such as mouse myeloma cells to give a humanized antibody-producing clone. The clone is checked whether it can produce the desired antibody by screening the culture supernatant of the clone by ELISA or the like. Thereafter, the clone being capable of producing effectively humanized antibody is cultured, and the humanized antibody thus produced is isolated and purified from the culture broth with a protein G column, etc. Finally, the antibody is subjected to gel filtration or dialysis to prepare a solution of the humanized antibody in a phosphate buffered saline solution.

The RA treating drug of the present invention is usally used in the form of an injection. The injection preparation can be prepared by a conventional method. That is, an injection preparation can be prepared by dissolving the monoclonal antibody obtained above in a phosphate buffered saline solution, and sterilizing the solution by filteration. The antibody-containing solution thus sterilized by filtration may be converted into a lyophylized product, which is dissolved when used.

The RA treating drug of the present invention can be administered, for example, by subcutaneous injection, intramuscular injection, intravenous injection, or intra-articular injection, preferably by intravenous or intra-articular injection. The dose of the RA treating drug of the present invention may vary in accordance with the symptoms, ages, weights of the RA patients, the kinds of the active antibody, the administration methods, and the like, but it is usually administered in a dose of 0.01 mg/kg to 10 mg/kg as an amount of the active antibody (a monoclonal antibody which recognizes specifically the extracellular region of human VLA-2) once a day, at a rate of once or twice in a week.

The monoclonal antibody used for the RA treating drug of the present invention can strongly inhibit the swelling due to arthritis in RA, and the antibody shows particularly strong activity, the highest among those of the monoclonal antibodies which can recognize specifically the extracellular region of adhesion molecule of human VLA family (cf. Experiments 1 and 2). Moreover, the monoclonal antibody used in the present RA treating drug can inhibit the swelling due to RA more strongly than a mixture of equal amount of anti-ICAM-1 antibody and anti-LFA-1 antibody, and more than anti-CD40L antibody (cf. Experiments 1 and 2).

The monoclonal antibody used in the present RA treating drug has low toxicity.

Accordingly, the RA treating drug of the present invention is useful for the treatment of RA.

The invention is illustrated by the following Experiments.

EXPERIMENT 1

Curing effects in mouse CIA model:

(1) Antibodies to be tested

Anti-VLA-2 antibody [hamster anti-mouse VLA-2 monoclonal antibody, clone: HMα2, manufactured by Sumitomo Electric Industries, Ltd. (SE-A1014)]

Anti-VLA-1 antibody [hamster anti-mouse VLA-1 monoclonal antibody, clone: HMα1, manufactured by Sumitomo Electric Industries, Ltd. (SE-A1013)] (reference antibody)

Anti-VLA-6 antibody [hamster anti-mouse VLA-2 monoclonal antibody, clone: HMα6, manufactured by Sumitomo Electric Industries, Ltd. (SE-A1015)] (reference antibody)

A mixture of equiamount of anti-ICAM-1 antibody [rat anti-mouse ICAM-1 monoclonal antibody, clone: KAT-1, manufactured by British Biotechnology (BSA2)] and anti-LFA-1 antibody [rat anti-mouse LFA-1 antibody, clone: KBA, manufactured by British Biotechnology (BSA5) (reference antibody)

(2) Test method

A solution of a bovine-origin type II collagen (4 mg/ml) in 0.05N acetic acid was mixed with an equiamount of Freund's complete adjuvant (DIFCO, FCA) and the mixture was emulsified. A mouse was sensitized with the emulsion by injecting it into the tail of a male DBA/1J mouse (8 weeks old, 5–10 mice per group) in an amount of 200 μg/mouse (as collagen). After three weeks, the animals were additionally immunized with an emulsion prepared by mixing the same collagen solution as above with an equiamount of Freund's incomplete adjuvant (DIFCO, FIA). From one day before the additional immunization, it was initiated to administer the test antibody to the mice intraperitoneally (dose per day, 250 μg/mouse, twice per week).

At 20th day after the sensitization, the degree of arthritis was evaluated by the following scores (0–4 points per each leg, total in for legs, 16 points at maximum)

(Score for arthritis)
  0 point: No change
  1 point: Wholly weak swelling or swelling on fingers
  2 point: Wholly light swelling
  3 point: Wholly clear swelling
  4 point: Wholly significant swelling (3) Test Results The test results are shown in the following Table 1. As is seen from Table 1, the group administered with the anti-VLA-2 antibody showed more significant suppression of swelling due to arthritis in comparison with the group administered with the anti-VLA-1 antibody, the group administered with the anti-VLA-6 antibody, and the group administered with a mixture of an equiamount of anti-ICAM-1 antibody and anti-LFA-1 antibody.

Besides, during this experiment, no toxic symptom (specific side effect, die, etc.) was observed in all animals administed with the test antibodies.

TABLE 1

| Test antibody | Change of score of arthritis | | | | | | | |
|---|---|---|---|---|---|---|---|---|
| | 20* | 23 | 27 | 30 | 34 | 37 | 41 | 44 | 48 |
| Anti-VLA-1 antibody | 0.0 | 0.0 | 0.4 | 1.1 | 3.1 | 4.2 | 6.7 | 7.4 | 8.5 |
| Anti-VLA-2 antibody | 0.0 | 0.0 | 0.8 | 1.5 | 2.2 | 2.7 | 4.5 | 5.0 | 4.8 |
| Anti-VLA-6 antibody | 0.0 | 0.0 | 1.2 | 4.3 | 4.9 | 5.9 | 6.9 | 6.1 | 7.1 |
| Anti-ICAM-1 antibody + Anti-LFA-1 antibody | 0.0 | 0.0 | 0.5 | 1.8 | 6.9 | 8.5 | 10.0 | 8.8 | 9.3 |
| Control | 0.0 | 0.0 | 1.0 | 2.8 | 5.0 | 7.6 | 8.6 | 10.4 | 11.0 |

*) Days after the first sensitization with collagen

EXPERIMENT 2

Curing effects in mouse CIA model:

(1) Antibodies to be tested

Anti-VLA-2 antibody [hamster anti-mouse VLA-2 monoclonal antibody, clone: HMα2, manufactured by Sumitomo Electric Industries, Ltd. (SE-A1014)]

Anti-VLA-4 antibody [rat anti-mouse VLA-4 monoclonal antibody, disclosed in Text Book of Immunology in Juntendo University, Faculty of Medicine] (reference antibody)

Anti-VLA-5 antibody [hamster anti-mouse VLA-5 monoclonal antibody, clone: HMα5-1, manufactured by Sumitomo Electric Industries, Ltd. (SE-A1002)] (reference antibody)

Anti-CD40L antibody [hamster anti-mouse CD40L monoclonal antibody, clone: HM40L-1, manufactured by Sumitomo Electric Industries, Ltd. (SE-A1020)] (reference antibody)

(2) Test method

The same as in Experiment 1

(3) Test Results

The test results are shown in the following Table 2. As is seen from Table 2, the group administered with the anti-VLA-2 antibody showed more significant suppression of swelling due to arthritis in comparison with the group administered with the anti-VLA-4 antibody, the group administered with the anti-VLA-5 antibody, and the group administered with the anti-CD40L antibody.

Besides, during this experiment, no toxic symptom (specific side effect, die, etc.) was observed in all animals administed with the test antibodies.

TABLE 2

| Test antibody | Change of score of arthritis | | | | | | | |
|---|---|---|---|---|---|---|---|---|
| | 20* | 23 | 27 | 30 | 34 | 37 | 41 | 44 | 48 |
| Anti-VLA-2 antibody | 0.0 | 0.6 | 0.5 | 1.0 | 1.8 | 1.8 | 2.2 | 2.1 | 2.2 |
| Anti-VLA-4 antibody | 0.0 | 0.0 | 0.4 | 1.0 | 1.9 | 2.9 | 4.2 | 4.7 | 6.8 |
| Anti-VLA-5 antibody | 0.0 | 0.1 | 0.1 | 0.3 | 2.1 | 2.6 | 3.5 | 3.0 | 3.6 |
| Anti-CD40L antibody | 0.0 | 0.1 | 0.3 | 0.5 | 1.4 | 2.9 | 4.8 | 4.6 | 5.4 |
| Control | 0.0 | 0.0 | 1.2 | 1.4 | 2.6 | 2.8 | 2.9 | 4.3 | 6.2 |

*) Days after the first sensitization with collagen

The present invention is illustrated by the following Examples.

EXAMPLE 1

Injection:

A solution of a monoclonal antibody which recognizes specifically extracellular region of human VLA-2 in a phosphate buffered saline solution (1 mg/ml) is sterilized by filtration and poured into ampoules in an amount of 5 ml per each ampoule to give injections containing the monoclonal antibody which recognizes specifically extra-cellular region of human VLA-2 (5 mg/ampoule).

EXAMPLE 2

Injection:

A solution of a monoclonal antibody which recognizes specifically extracellular region of human VLA-2, a chain in a phosphate buffered saline solution (1 mg/ml) is sterilized by filtration and poured into ampoules in an amount of 5 ml per each ampoule to give injections containing the monoclonal antibody which recognizes specifically extracellular region of human VLA-2, α chain (5 mg/ampoule).

We claim:

1. A method for treating rheumatoid arthritis, comprising administering to a patient a pharmaceutical composition comprising an effective amount for treating rheumatoid arthritis of a monoclonal antibody which specifically recognizes an extracellular region of human VLA-2 in combination with a pharmaceutically acceptable carrier.

2. The method according to claim 1, wherein the carrier is phosphate buffered saline.

3. The method according to claim 1, wherein the monoclonal antibody is a humanized antibody.

4. The method according to claim 1, wherein the monoclonal antibody is a mammalian anti-human antibody.

5. The method according to claim 1, wherein the monoclonal antibody is a chimeric antibody comprising a human antibody constant region and a non-human antibody variable region.

6. The method according to claim 1, wherein the monoclonal antibody specifically recognizes an $\alpha$ chain of human VLA-2.

* * * * *